United States Patent [19]

Kersting et al.

[11] 4,266,962
[45] May 12, 1981

[54] DRIFT REDUCING AGRICULTURAL COMPOSITIONS

[75] Inventors: Elmar Kersting, Stolberg; Heinz J. Niessen, Berg. Gladbach, both of Fed. Rep. of Germany

[73] Assignee: Bayer Aktiengesellschaft, Leverkusen, Fed. Rep. of Germany

[21] Appl. No.: 575,316

[22] Filed: May 7, 1975

[30] Foreign Application Priority Data

May 11, 1974 [DE] Fed. Rep. of Germany ....... 2422954

[51] Int. Cl.$^3$ .................... A01N 43/74; A01N 37/10; A01N 37/38; A01N 57/28
[52] U.S. Cl. .......................... 71/90; 71/103; 71/107; 71/116; 71/117; 71/DIG. 1; 424/171; 424/220; 424/324
[58] Field of Search ...................... 71/DIG. 1, 65, 108, 71/109, 87, 90, 107, 116, 117, 103; 424/220, 320, 171, 324

[56] References Cited

U.S. PATENT DOCUMENTS

| | | | |
|---|---|---|---|
| 3,172,750 | 3/1965 | Altscher et al. | 71/DIG. 1 |
| 3,231,363 | 1/1966 | Renner | 71/DIG. 1 |
| 3,869,276 | 3/1975 | Priola et al. | 71/DIG. 1 |
| 4,102,667 | 7/1978 | Robinson et al. | 71/DIG. 1 X |

FOREIGN PATENT DOCUMENTS 524025  4/1956  Canada ................................ 71/DIG. 1

Primary Examiner—Joseph Paul Brust
Attorney, Agent, or Firm—Sprung, Felfe, Horn, Lynch & Kramer

[57] ABSTRACT

The drifting tendency of agricultural chemical spraying liquids, particularly aqueous spraying liquids, is reduced by adding thereto as a foaming agent an amine salt of a p-alkylbenzenesulfonic acid of the general formula

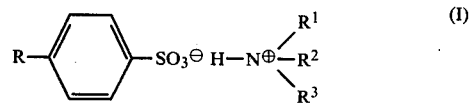 (I)

in which
  R is alkyl of from 8 to 16 carbon atoms,
  $R^1$ and $R^2$ (which may be the same or different) are hydrogen, alkyl, or hydroxyalkyl of from 1 to 6 carbon atoms, and
  $R^3$ is alkyl or hydroxyalkyl of from 1 to 6 carbon atoms.

18 Claims, No Drawings

DRIFT REDUCING AGRICULTURAL COMPOSITIONS

The present invention relates to a crop protection composition and to a method of application, whereby the drift of spraying liquids may be reduced. The invention is particularly applicable to aqueous spraying liquids.

Pesticidal active compounds are often sprayed, especially in the form of aqueous spraying liquids, on to plants or their habitat. On applying such spraying liquids, a more or less pronouced drifting off of the liquid active compound preparation used may be observed, depending on the particular prevailing wind conditions. This drifting off is extremely undesirable because it causes a certain part of the amount of plant protection agent employed to be lost as far as the intended application on the area actually to be treated is concerned. Furthermore, the drifting off of a part of the active compound sprayed can under certain circumstances have the effect of damaging plant crops which are in the immediate vicinity of the intended application zones. Furthermore, the pesticides which drift off can, particularly where strongly toxic compounds are concerned, constitute a hazard to persons or animals, for example the persons who apply the spraying liquid.

It has already been proposed to reduce the drift when applying aqueous spraying liquids of plant protection agents by adding foaming agents to the spraying liquid. Thus, a product obtainable from Colloidal Products Corp. (Petaluma, Calif., USA) under the trade name "Fomex", which consists of a mixture of alcohol sulfates, salts of alkyl- and dialkyl-2,5-diketo-tetrahydrofuran, alkylsulfonates, isopropanol and water, can be used as such a foaming agent having a drift-reducing action. However, it is a disadvantage of the use of this agent that it must be present in relatively high concentrations, that is to say in a concentration over 0.5 percent by volume, in the spraying liquid which is to be applied. It is a further disadvantage that even if this foaming agent is present in such high concentrations in the aqueous spraying liquid, the drift-reducing action of the agent is not always sufficient for practical purposes.

The present invention comprises the use of known amine salts of p-alkylbenzenesulfonic acids as foaming agents, so as to reduce the drift, especially when spraying aqueous spraying liquids of plant protection agents. More specifically, the present invention provides a crop protection composition containing an active crop protection agent and, as a foaming agent, an amine salt of a p-alkylbenzenesulfonic acid of the general formula.

$$R-\!\!\!\left\langle\!\!\begin{array}{c}\phantom{x}\\\phantom{x}\end{array}\!\!\right\rangle\!\!-SO_3^{\ominus}\ H-N^{\oplus}\!\!\begin{array}{c}R^1\\ -R^2\\ R^3\end{array} \quad (I)$$

in which
R is alkyl of from 8 to 16 carbon atoms,
$R^1$ and $R^2$ (which may be the same or different) are hydrogen, alkyl, or hydroxyalkyl of from 1 to 6 carbon atoms, and
$R^3$ is alkyl or hydroxyalkyl of from 1 to 6 carbon atoms.

The invention also provides a method of applying an active crop protection agent to a crop area which comprises spraying a composition according to the invention on to the area.

Surprisingly, the use according to the invention of the amine salts of p-alkylbenzenesulfonic acid in spraying liquids, especially aqueous spraying liquids, of plant protection agents achieves a substantially better reduction in drift when applying such spraying liquids than when adding the same quantity of the product obtainable commercially under the name Fomex which is recognized to be a very effective agent for the stated end use. Hence, a smaller amount of the compounds usable according to the invention than of standard agents suffices to achieve the same drift-reducing effect. This fact is of considerable importance, for example for environmental protection reasons. The use of the foaming agents according to the invention thus represent a valuable enrichment of the art.

The formula (I) provides a general definition of the amine salts of p-alkylbenzenesulfonic acids which can be used according to the invention. In the formula (I), R preferably represents straight-chain alkyl with 10 to 14, carbon atoms. $R^1$ and $R^2$ (which may be the same or different) preferably represent hydrogen, straight-chain or branched alkyl with 1 to 4 carbon atoms, amongst which 2-hydroxyethyl should be mentioned especially. $R^3$ preferably represents straight-chain or branched alkyl with 1 to 4 carbon atoms or straight-chain or branched hydroxyalkyl with 1 to 4 carbon atoms, amongst which 2-hydroxyethyl should be mentioned especially.

The following may be mentioned individually as examples of the compounds which can be used according to the invention: mono-ethanolammonium (4-n-dodecyl)-benzenesulfonate, diethanolammonium (4-n-dodecyl)-benzenesulfonate, tri-ethanolammonium (4n-dodecyl)-benzenesulfonate, mono-ethanolammonium (4-n-tetradecyl)-benzenesulfonate, di-ethanolammonium (4-n-tetradecyl)-benzenesulfonate, or tri-ethanolammonium (4-n-tetradecyl)-benezenesulfonate.

The amine salts of p-alkylbenezenesulfonic acids to be used according to the invention are known or can be prepared in a simple manner in accordance with known methods (compare Houben-Weyl, Volume 1/2, 118 to 120 (1959). However, their use as foaming agents to reduce the drift when applying aqueous spraying liquids of plant protection agents is new.

These compounds have surface-active properties and can therefore function as foaming agents. They have surprisingly been found to be outstandingly suitable for greatly lowering the undesired drift when spraying aqueous spraying liquids of plant protection agents. For this purpose, the compounds which can be used according to the invention are preferably added in the form of solutions to the spraying liquids to be applied. However, it is also possible to add the amine salts of p-alkylbenzenesulfonic acids directly to the ready-to-use spraying liquid.

Solutions of the amine salts of p-alkylbenzenesulfonic acids which can be used according to the invention can be prepared according to customary methods, that is to say, for example, by mixing the foaming agents with one or more solvents. Solvents which can be used for this purpose are all solvents which adequately dissolve the foaming agents, which are futhermore miscible with water, which in addition do not adversely affect the foaming and which, finally, are safe from a toxicological point of view and with regard to their effect on the environment. Preferred solvents include alcohols, both monovalent alcohols, such as ethanol, n-propanol and isopropanol, and polyhydric alcohols, such as ethylene glycol, as well as water.

If the compounds which can be used according to the invention are to be admixed as solutions with the aqueous spray liquors, the concentrations of foaming agents in these solutions can be varied within substantial ranges. In general, solutions in which the concentrations of foaming agents are between 20 and 70 percent by weight, preferably between 40 and 60 percent by weight, are used.

In the ready-to-use aqueous spraying liquids, the concentrations of foaming agents according to the invention can also be varied within substantial ranges. In general, the concentrations are between 0.25 and 0.65 percent by volume, preferably between 0.35 and 0.55 percent by volume.

The materials or solutions usable according to the invention, which contain these compounds, can be admixed with all aqueous spraying liquids of plant protection agents customary in agriculture.

Plant protection agents are to be understood as including, for example fungicidal, insecticidal, herbicidal, acaricidal, rodenticidal, avicidal, and/or molluscicidal agents.

As examples of special aqueous spraying liquids with which the foaming agents usable according to the invention can be admixed there may be mentioned spray liquors which contain any of the following active crop protection agents: 3-(4'-chlorophenyl)-2-chloropropionic acid methyl ester, 4-chloro-2-methylphenoxyacetic acid, 2,4-dichlorophenoxyacetic acid, 2-(2,4-dichlorophenoxy)-propionic acid, N-formyl-N'-3,4-dichlorophenyl-trichloro-acetaldehyde-aminal, O,S-dimethyl-amidothiophosphate and N-(2-benzthiazolyl)-N,N'-dimethylurea. Aqueous plant protection spraying liquids with which foaming agents according to the invention are admixed in order to reduce the drift, should be applied to the plants, or their habitat, with the aid of special spray nozzles. Such nozzles, which permit foaming when applying spray liquors, are already known (compare Foam, Farm Chemicals 135, No. 5, 13 to 20 (1972)).

From what has been stated above, it will be seen that the composition of the invention is preferably in an aqueous medium, and that the medium may comprise a non-aqueous but water-miscible solvent for the amine salt, such as an alcohol.

The invention also provides a method of applying a crop protection agent to a crop area which comprises spraying a composition according to the invention on to the area.

The preparation and advantageous mode of action of the compounds to be used according to the invention as foaming agents for reducing the drift when applying aqueous spray liquors of plant protection agents is illustrated by the examples which follow.

EXAMPLE 1

Preparation of the foaming agent 7.9 kg (129.5 moles) of monoethanolamine were allowed to run into a suspension of 42.1 kg (129.1 moles) of 4-(n-dodecyl)-benzenesulfonic acid in 27.5 liters of water, with stirring and moderate cooling. 22.3 liters of isopropanol and 4.5 liters of ethylene glycol were then added and the mixture was stirred until a homogeneous solution had been produced.

A solution which contained mono-ethanolammonium (4-n-dodecyl)-benzenesulfonate in a concentration of 50 percent by weight was obtained.

EXAMPLE 2

Determination of the drift

Spraying experiments were carried out in a climatically controlled chamber 15 m long, 2.5 m wide and 2.5 m high, at an air temperature of 20° C. and 60% atmospheric humidity. For these experiments, an axial fan ($\phi$ 400 mm; output 4,200 $m^3$/hour) having a 2 m long streamlining zone built on to it, was mounted, at the entrance to the chamber, in such a way that the center of the air stream produced was 50 cm above the floor. At a distance of 30 cm from the streamlining zone, a special nozzle for foaming of aqueous spraying liquids mounted in the center of the air stream, at a height of 50 cm above the floor.

To carry out the experiments, an aqueous spraying liquid which contained 0.5% of a foaming additive was passed under a constant pressure of 2.5 bars from a reservoir to the nozzle and was foamed at various defined wind velocities. The foamed spraying liquid was collected on glass plates of size 10×10 cm, which were set up parallel to the air stream at intervals of about 25 cm at a distance of 12 m from the fan. The spraying time was 15 seconds in each experiment. Immediately after completion of an experiment, the glass plates were examined for traces of foam.

The drift was determined by measuring the distance of the glass plate furthest remote from the nozzle which still showed traces of foam and expressing the values in percent. 100% denotes the drift observed when foaming the spray liquor to which the standard agent Fomex had been added. 0% denotes that no drift was detected.

The following spraying liquids were used:

Spraying liquid A=aqueous spraying liquid to which 0.5% of the standard agent Fomex had been admixed.

Spraying liquid B=aqueous spraying liquid to which 0.5% of mono-ethanolammonium (4-n-dodecyl)-benzenesulfonic (compare Example 1) had been mixed.

The results obtained at the various wind velocities are shown in Table 1 below.

TABLE 1

| Wind velocity [m/sec] | Drift when using spraying Liquid A % | Drift when using spraying Liquid B % | Drift advantage when using spraying liquid B % |
|---|---|---|---|
| 1 | 100 | 86 | 14 |
| 2 | 100 | 85 | 15 |
| 3 | 100 | 84 | 16 |
| 4 | 100 | 84 | 16 |
| 5 | 100 | 83 | 17 |
| 6 | 100 | 82 | 18 |

The results listed in Table 1 are each average values from three experiments.

EXAMPLE 3

Toleration test and action test (a) Various plant crops were sprayed, in a greenhouse, with a customary aqueous spray liquor and with an aqueous spraying liquid to which 0.5% of monoethylammonium (4-n-dodecyl)-benzenesulfonate had been admixed as a foaming agent.

The experimental results showed that the customary aqueous spraying liquid and the spraying liquid containing foaming agent do not differ with regard to their toleration by plants.

(b) Weeds in cereals were combated, in the open, with the spraying liquids mentioned below.

Spraying liquid A=customary aqueous spraying liquid which contained N-(2-benzthiazolyl-N,N'-dimethylurea as the herbicidal active agent.

Spraying liquid B=aqueous spraying liquid which contained N-(2-benzthiazolyl)-N,N'-dimethylurea as the herbicidal active agent and 0.5% of monoethanolammonium (4-n-dodecyl)-benzene-sulfonate as the foaming agent.

An evaluation of the experimental results showed that the foaming agent impairs neither the effectiveness of the herbicidal active compound nor the harvest yields.

(c) Cereal mildew (*Erysiphe graminis*) was combated in the open with the spraying liquids mentioned below.

Spraying liquid A=customary aqueous spraying liquid which contained N-formyl-N'-3,4-dichlorophenyl-trichloroacetalde-hyde-aminal as the fungicidal active agent.

Spraying liquid B=aqueous spraying liquid which contained N-formyl-N'-3,4-dichlorophenyl-trichloroacetaldehyde-aminal as the fungicidal active agent and 0.5% of monoethanol-ammonium (4-n-dodecyl)-benzenesulfonate as the foaming agent.

An evaluation of the results showed that the effectiveness of the fungicidal active compound is in no way impaired by the foaming agent.

(d) The European corn borer (*Pyrausta nubilalis*) was combated in the open with the spraying liquids mentioned below.

Spraying liquid A=customary aqueous spraying liquid which contained O,S-dimethyl-amido-thiophosphate as the insecticidal active agent.

Spraying liquid B=aqueous spraying liquid which contained O,S-dimethyl-amido-thiophosphate as the insecticidal active agent and 0.5% of monoethanolammonium (4-n-dodecyl)-benzenesulfonate as the foaming agent.

The evaluation of the results showed that the effectiveness of the insecticidal active compound is in no way impaired by the foaming agent.

It will be understood that the specification and examples are illustrative but not limitative of the present invention and that other embodiments within the spirit and scope of the invention will suggest themselves to those skilled in the art.

What is claimed is:

1. Method of reducing the drift of sprayed agricultural chemical compositions which method comprises applying to an area of vegetation a crop protection composition containing an active crop protection agent and, as a foaming agent, an amine salt of a p-alkylbenzenesulfonic acid of the general formula.

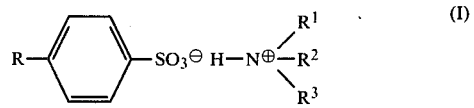

in which

R is alkyl of from 8 to 16 carbon atoms.

$R^1$ and $R^2$ are individually selected from hydrogen, alkyl, or hydroxyalkyl of from 1 to 6 carbon atoms, and $R^3$ is alkyl or hydroxyalkyl of from 1 to 6 carbon atoms.

2. A method as claimed in claim 1 wherein R is alkyl of from 10 to 14 carbon atoms.

3. A method as claimed in claim 1 wherein at least one of $R^1$ and $R^2$ is alkyl of from 1 to 4 carbon atoms.

4. A method as claimed in claim 1 wherein at least one of $R^1$ and $R^2$ is 2-hydroxyethyl.

5. A method as claimed in claim 1 wherein $R^3$ is alkyl of from 1 to 4 carbon atoms.

6. A method as claimed in claim 1 wherein $R^3$ is hydroxyalkyl of from 1 to 4 carbon atoms.

7. A method as claimed in claim 6 wherein $R^3$ is 2-hydroxyethyl.

8. A method as claimed in claim 1 wherein the amine salt is at least one of mono-ethanolammonium (4-n-dodecyl)-benzenesulfonate, di-ethanolammonium (4-n-dodecyl)-benzenesulfonate, tri-ethanolammonium (4-n-dodecyl)-benzenesulfonate, monoethanolammonium (4-n-tetradecyl)-benzenesulfonate, di-ethanolammonium (4-n-tetradecyl)-benzenesulfonate or tri-ethanolammonium (4-n-tetradecyl)-benzenesulfonate.

9. A method as claimed in claim 1 wherein the amine salt is mono-ethanolammonium (4-n-dodecyl)-benzenesulfonate.

10. A method as claimed in claim 1 wherin the amine salt is di-ethanolammonium (4-n-dodecyl)-benzenesulfonate.

11. A method as claimed in claim 1 wherein the amine salt is tri-ethanolammonium (4-n-dodecyl)-benzenesulfonate.

12. A method as claimed in claim 1 wherein the amine salt is mono-ethanolammonium (4-tetradecyl)-benzenesulfonate.

13. A method as claimed in claim 1 wherein said composition is an aqueous medium.

14. A method as claimed in claim 13 wherein the medium also comprises a water-immiscible solvent for the amine salt.

15. A method as claimed in claim 14 wherein said non-aqueous water-immiscible solvent is an alcohol.

16. Method as claimed in claim 1 wherein the composition contains 0.25 to 0.65 percent by volume of the amine salt.

17. Method as claimed in claim 16 wherein the spray composition contains 0.35 to 0.55 percent by volume of the amine salt.

18. Method as claimed in claim 16 wherein the amine salt is at least one of mono-ethanolammonium (4-n-dodecyl)-benezenesulfonate, di-ethanolammonium (4-n-dodecyl)-benzenesulfonate, tri-ethanolammonium (4-n-dodecyl)-benzenesulfonate, monoethanolammonium (4-n-tetradecyl)-benzenesulfonate, di-ethanolammonium (4-n-tetradecyl)-benzenesulfonate or tri-ethanolammonium (4-n-tetradecyl)-benzenesulfonate.

* * * * *